(12) United States Patent
Satake et al.

(10) Patent No.: US 6,629,842 B2
(45) Date of Patent: Oct. 7, 2003

(54) DENTAL HANDPIECE

(75) Inventors: Nozomu Satake, Takanezawa-machi (JP); Toshiyuki Takase, Takanezawa-machi (JP)

(73) Assignee: Mani, Inc., Tochigi (JP)

( * ) Notice: Subject to any disclaimer, the term of this patent is extended or adjusted under 35 U.S.C. 154(b) by 25 days.

(21) Appl. No.: 09/923,206

(22) Filed: Aug. 6, 2001

(65) Prior Publication Data

US 2002/0025504 A1 Feb. 28, 2002

(30) Foreign Application Priority Data

Aug. 29, 2000 (JP) ........................................ 2000-258793

(51) Int. Cl.[7] .............................. A61C 1/08; A61C 3/00
(52) U.S. Cl. ....................................... 433/105; 433/122
(58) Field of Search ................................. 433/105, 122, 433/123

(56) References Cited

U.S. PATENT DOCUMENTS

| | | | | |
|---|---|---|---|---|
| 3,986,634 A | * | 10/1976 | Smith et al. ................ | 220/288 |
| 4,976,625 A | * | 12/1990 | Weissman ................... | 433/118 |
| 5,924,864 A | * | 7/1999 | Loge et al. .................. | 433/118 |
| 6,106,290 A | * | 8/2000 | Weissman ................... | 433/118 |

* cited by examiner

Primary Examiner—John J. Wilson
(74) Attorney, Agent, or Firm—Muramatsu & Associates

(57) ABSTRACT

A dental handpiece to securely detect the load applied to the handpiece itself, and when an excessive load is applied to the handpiece, the cutting operation is suspended. The dental handpiece includes: a head; a support mounted in the head to support a cutting tool; and a transmission mounted in the head to transmit driving force to the support. The support and the transmission are slidably connected with each other. In the dental handpiece, the support may be cylindrical and can be provided with a plurality of inclined projections that are arranged in a longitudinal direction of an outer periphery of the cylinder; the transmission may be provided with engaging projections with inclined faces parallel to inclined faces of the plurality of inclined projections; and the transmission can be provided with resiliency that allows the engaging projections movable in a direction departing from the inclined projections.

8 Claims, 10 Drawing Sheets

DENTAL HANDPIECE

BACKGROUND OF THE INVENTION

1. Field of the Invention

The present invention relates to a handpiece for dental use, and more particularly, to a handpiece to be used by a dentist for cutting or drilling a root canal of a tooth.

2. Description of the Related Art

In curing a root canal of a tooth, a cutting tool such as a dental reamer or a dental file with an edge is generally used to form a root canal. These cutting tools are provided with a spiral cutting edge, and the edge portion is inserted into a root canal, and then, the back and forth movements or rotational movements of the cutting tools by changing the cutting tools corresponding to the shape of the root canal allows the root canal to be tapered. To cut a root canal, a handle of a cutting tool is held for manual operation, or a cutting tool is connected to a dental handpiece for using rotationally driving force of an engine such as a motor.

Since a dental reamer has a large lead, that is, a relatively gentle spiral cutting edge, it is mainly used for cutting by rotational movements. In contrast, a dental file has a spiral cutting edge having a lead smaller than that of the dental reamer; therefore, it is mainly used for cutting through back and forth movements like a file. Further, the dental file is often used by incorporating the back and forth movements as well as some rotational movements at the same time, which allows a root canal to be cut by the back movement and debris generated by the cutting to be carried away to outside of the root canal through spiral channels of the edge portion. "The cutting" means that an edge portion of a cutting tool enters the wall of a root canal to some extent, and a part of the wall is scraped off. However, if the edge portion of the cutting tool excessively enters the wall, it becomes impossible to perform the cutting operation.

A dental handpiece heretofore in use for operating these cutting tools is sometimes capable of driving the tools by back and forth movements, by rotational movements, or by both the back and forth movements and the rotational movements. A dental handpiece is generally driven by an engine such as a motor, thus, a type of a transmission which transmits the driving force to the cutting tools and a manner that the transmission rotates decide the movement of the cutting tool either the back and forth movements or the rotational movements only, or both the back and forth movements and the rotational movements.

In the cutting with driving force from an engine, the rotation of a motor is transformed to the back and forth movements or the rotational movements and is applied to a cutting tool through a transmission, and the cutting tool cuts the wall of a root canal, and the cutting tool is pushed toward a root apex to form the root canal. Therefore, in the cutting operation, there is a problem that excessive force is applied to the cutting tool, even if the tool size is larger than that of a root canal to be cut, the cutting tool proceeds deep into the root canal while entering the wall thereof, and then the cutting tool is deformed or broken due to the excessive cutting.

Further, as shown in FIGS. 9A and 9B, there is a problem of creating a ledge in the root canal. FIGS. 9A and 9B show that a ledge is formed in a root canal $1a$ of a tooth 1 to be cured. As illustrated in FIG. 9A, the root canal $1a$ is curved. When a cutting tool 2 inserted into the root canal $1a$ can not follow the curved root canal $1a$ smoothly due to the insufficient resiliency, and the further rotational movements or back and forth movements are added to the cutting tool 2, a ledge shown in FIG. 9B is formed. As a result, it becomes impossible to form a root canal along the curve.

In addition to the above, as shown in FIGS. 10A and 10B, the root canal $1a$ is tapered toward its root apex, as illustrated in FIG. 10A, if the diameter of the cutting tool 2 is too large in relation to that of the root canal, the cutting tool 2 must be changed to a thinner cutting tool 2' to cut the root canal. Generally, it is required to change the cutting tools several times to form one root canal. However, in a dental handpiece driven by a motor in the conventional technology, it is difficult to appropriately know the timings to change the cutting tools. Therefore, when the timing to change the cutting tools is advanced to prevent the breakage of the cutting tool or the generation of the ledge, there is a problem that the formation of the root canal becomes insufficient since the cutting tool in operation is too thin.

When a ledge is formed, a cutting tool will not cut along a root canal, which causes a problem where a large force is applied to the cutting tool. When a thick cutting tool is used to cut a thin root canal also, a large force is applied to the cutting tool. That is, the above-mentioned problems arise because a large load that is applied to a cutting tool cannot be controlled; therefore, in case that an excessive load is applied to a cutting tool, it is necessary to suspend the cutting operation.

In consideration of the above problems, a dental handpiece with a mechanism for controlling torque in a driving connection has been proposed in Japanese Patent Application Laid-open Heisei 10-314185. In this dental handpiece, a coupling for preventing an excessive load is mounted in the driving connection to drive a cutting tool, and when the excessive load is applied to the cutting tool, resultant slippage produced in the coupling suspends the cutting operation by the cutting tool.

However, since the coupling for preventing the excessive load is mounted at a place in the driving connection, which is far from the cutting tool, it is difficult to detect the change of the load applied to the cutting tool itself. In other words, the load applied to the coupling is the sum of a load applied to the cutting tool and a load applied to a transmission including a drive shaft and a bearing, thus it is difficult to distinguish whether an edge portion of the cutting tool excessively enters a wall of a root canal or the resistance of the drive shaft increases. Therefore, even if a threshold level of the load that the cutting tool should be slipped is set, it is practically impossible to appropriately judge the timing to change the cutting tools or the like.

It is therefore an object of the present invention to improve the above dental handpiece and provide a dental handpiece to securely detect the load applied to the handpiece itself, and when an excessive load is applied to the handpiece, the cutting operation is suspended. To accomplish the above objective, a dental handpiece according to the present invention comprises: a head; a support mounted in the head to support a cutting tool; and a transmission mounted in the head to transmit driving force to the support; wherein the support and the transmission are slidably connected with each other.

In the above dental handpiece, preferably, the support is cylindrical and is provided with a plurality of inclined projections that are arranged in a longitudinal direction of an outer periphery of the cylinder; the transmission is provided with engaging projections with inclined faces parallel to inclined faces of the plurality of inclined projections; and the transmission is provided with resiliency that allows the engaging projections movable in a direction departing from the inclined projections.

In the above dental handpiece, it is preferable to provide a plurality of inclined projections with inclined faces different from those of the inclined projections at positions different from those of the inclined projections; and the transmission engages with one selected from two groups of inclined projections. In this construction, it is preferable that one of the groups of inclined projections engages with the transmission only in one direction and is always slidable in relation to the transmission in a direction opposite to the one direction. In addition, another group of projections engage with the transmission only in a direction reverse to the above. As a result of the above construction, the transmission is preferably movable to a desired position by changing an angle relative to the support.

Besides, it is possible to form the dental handpiece according to the present invention in such a manner that the support is cylindrical and is provided with a ratchet gear at an outer periphery thereof; the dental handpiece further comprises an inner ratchet engaging with the ratchet gear, a rotation transmitting means for rotating the inner ratchet and a rotationally driving means for driving the rotation transmitting means; and the inner ratchet is resiliently displaceable in a direction that an engagement with the ratchet gear is released. The rotation transmitting means and the rotationally driving means may be bevel gears that engage with each other.

With the dental handpiece described above, the wall of a root canal is cut by the cutting tool with rotational movements and back and forth movements. When the cutting tool cuts only one portion (a portion out of convex canal) and a ledge is about to be formed, the load applied to the cutting tool becomes large, so that the cutting tool slips, which prevents further cutting operation. In addition, when the diameter of a root canal becomes small, and the diameter of the cutting tool becomes large relative to the root canal, load applied to the cutting tool becomes large, so that the cutting tool slips, which prevents further cutting operation. As a result, it is possible to know the timing that the cutting tool should be changed. Like this, the dental handpiece of the present invention is characterized in that the rate that the energy from a motor is transmitted can be changed in accordance with the load applied to the cutting tool. In other words, when the load becomes large, slippage occurs between the support and the transmission, which intentionally weaken the motion of the cutting tool. Thus, in this invention, rather than by a driving source such as a motor, the slippage is produced through a mechanical structure such as the connection between the support and the transmission.

Without the slippage in dental handpieces in the past, the above problems frequently occur, and the control mainly relies upon the sense of a dentist, which is a burden to the dentist. With the present invention, mechanical control is achieved, resulting in a safe enlarging operation of a root canal. Especially, with the construction according to the present invention, a slipping mechanism is mounted to a head near the object to be cured, thus it becomes possible to quickly detect an excessive increase of load due to catching of a cutting tool.

BRIEF DESCRIPTION OF THE DRAWINGS

The present invention will be more apparent from the ensuring description with reference to the accompanying drawings wherein:

FIG. 5A is a cross-sectional view observed from E—E of FIG. 5C,

FIG. 5B is a front view and

FIG. 5C is a top view;

FIG. 6A is a longitudinally cross-sectional view and

FIG. 6B is a bottom view;

FIG. 7A is a cross-sectional view observed from F—F of FIG. 7B, and FIG. 7B is a longitudinally cross-sectional view;

FIG. 8A shows a movement in an ordinary cutting operation, FIG. 5B shows a movement when the support is lifted to change the cutting tool, and FIG. 8C shows a movement when the new cutting tool is lowered to a desired position;

DETAILED DESCRIPTION OF PREFERRED EMBODIMENTS

The dental handpiece according to the present invention will be described in detail with reference to the accompanying drawings wherein like numerals refer to like parts throughout.

Figure 1:
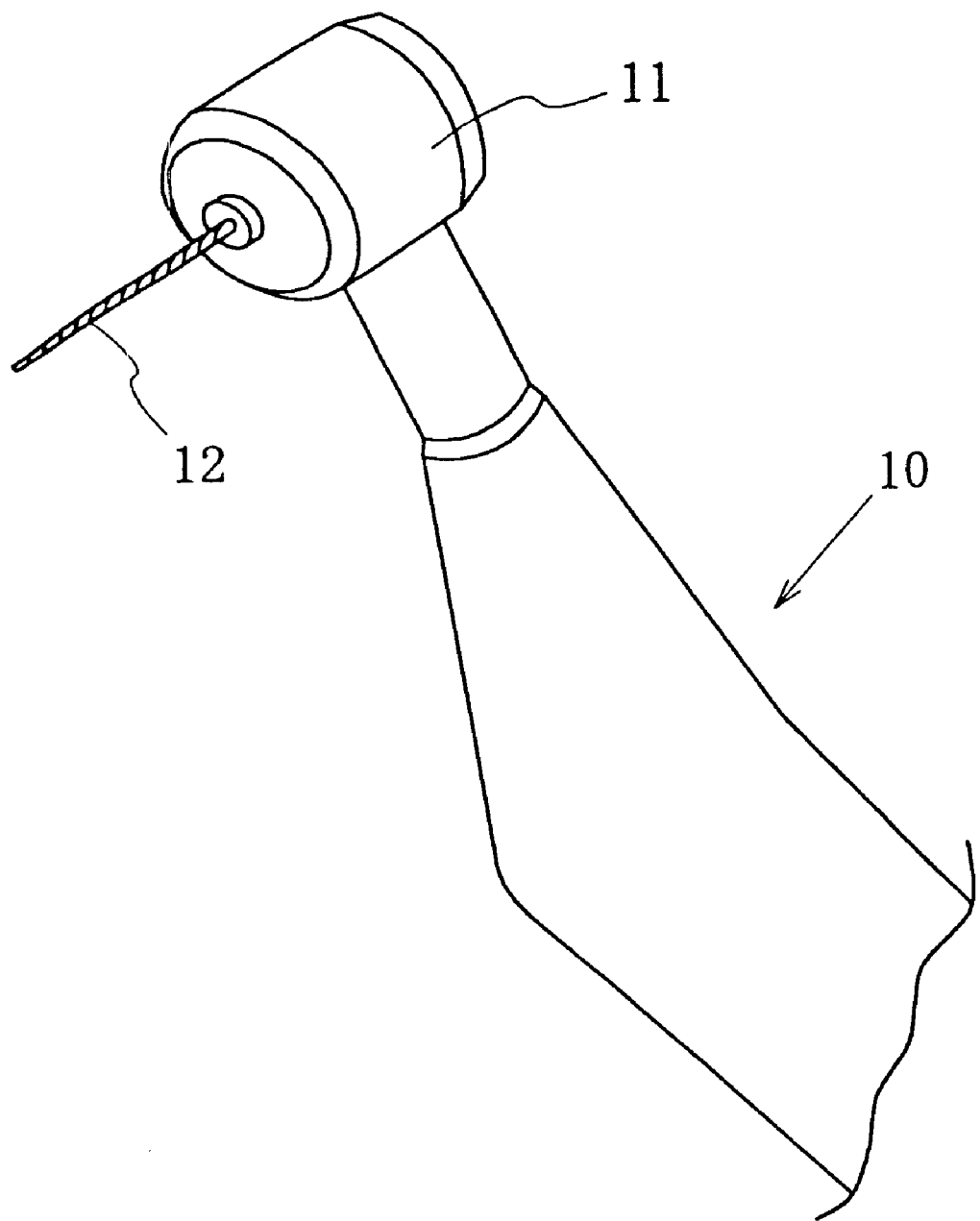
FIG. 1 is a perspective view of a primary potion of a dental handpiece according to one embodiment of the present invention.

The perspective view of FIG. 1 shows a primary portion of the dental handpiece of the present invention. In the dental handpiece 10 illustrated in the figure, a cutting tool 12 is attached to a head 11 at the tip of the dental handpiece 10.

Figure 2:
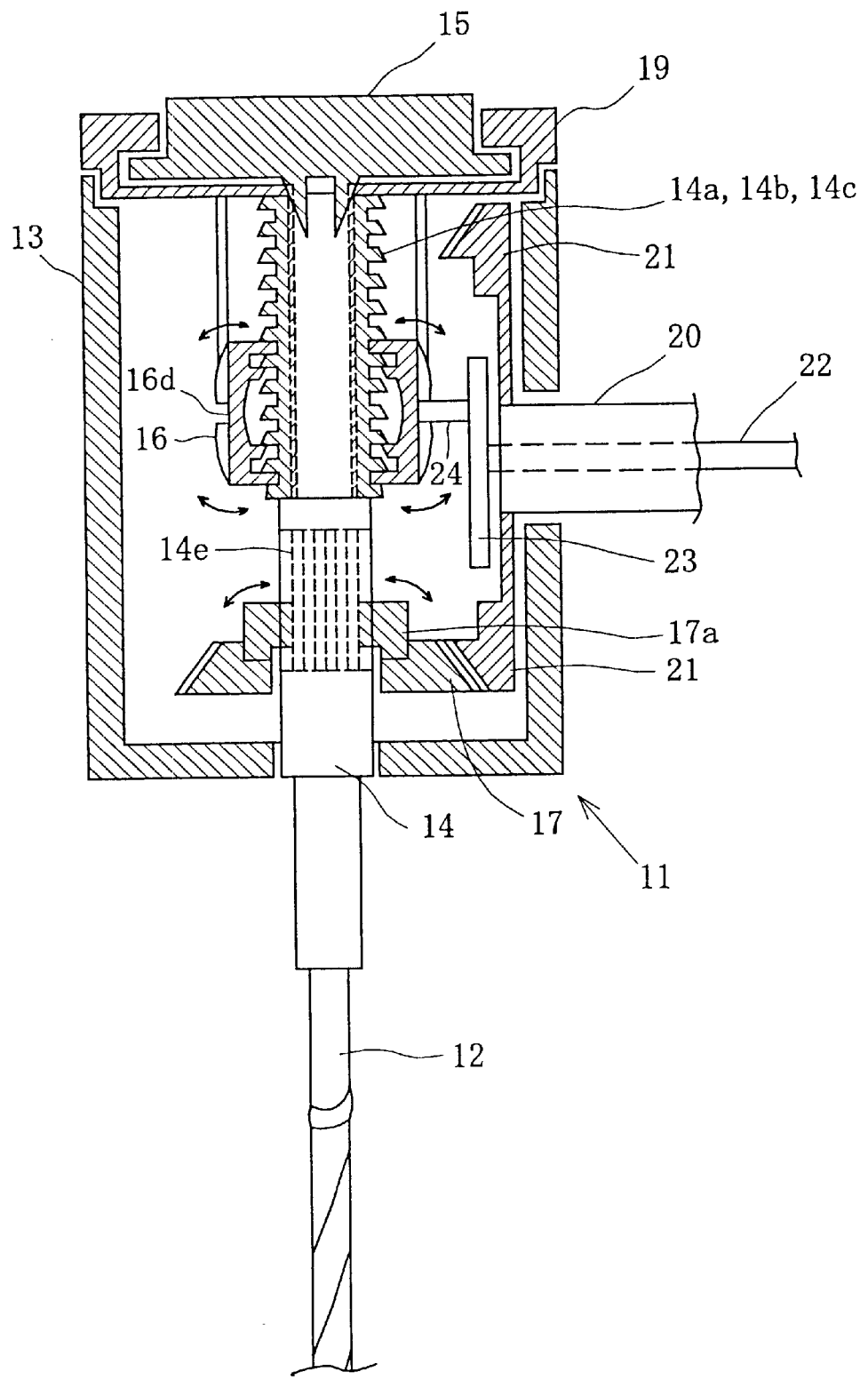
FIG. 2 is a cross-sectional view of a head of the dental handpiece.

FIG. 2 is a cross-sectional view of the head 11. A bearing not shown supports a hollow and cylindrical support 14 so as to be rotatable about the central axis thereof. Into the support 14 is inserted a cutting tool 12 such as a file and a reamer from the bottom of FIG. 2, and the cutting tool 12 is engaged with an engaging portion not shown at a portion above the support 14 so as not to be dropped. At the upper end of the support 14 is provided a push button 15, and depressing the push button 15 in the FIG. 2 allows the engagement of the cutting tool 12 and the support 14 to be released to remove the cutting tool 12 from the support 14. When the cutting tool 12 engages with the support 14, the cutting tool 12 and the support 14 are integral with each other at the rotational movement and the back and forth movements.

Figure 3A:
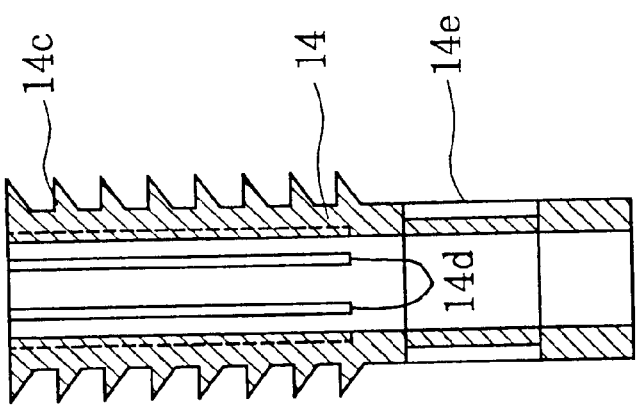
FIGS. 3A to 3C are cross-sectional views showing inclined projections and inversely inclined projections of a support.
Figure 3B:
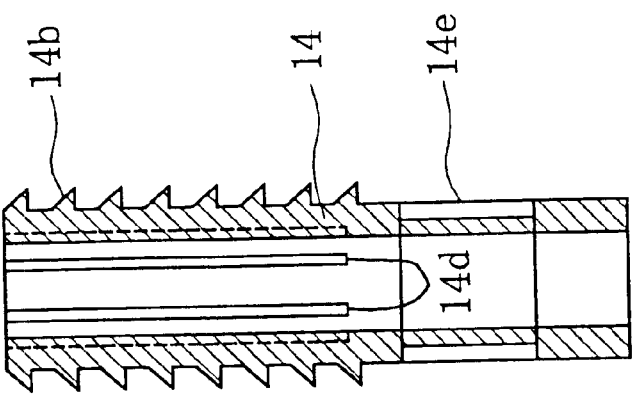
Figure 3C:
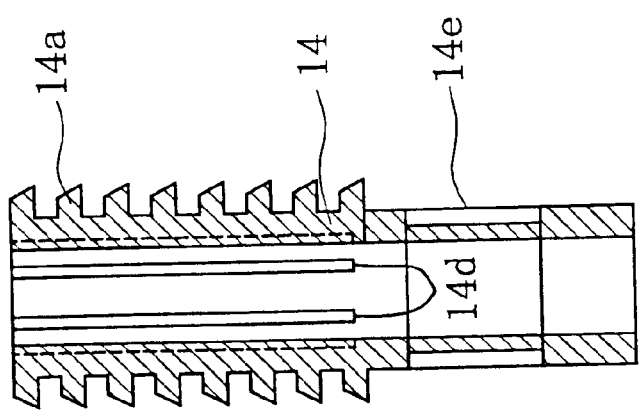
Figure 4:
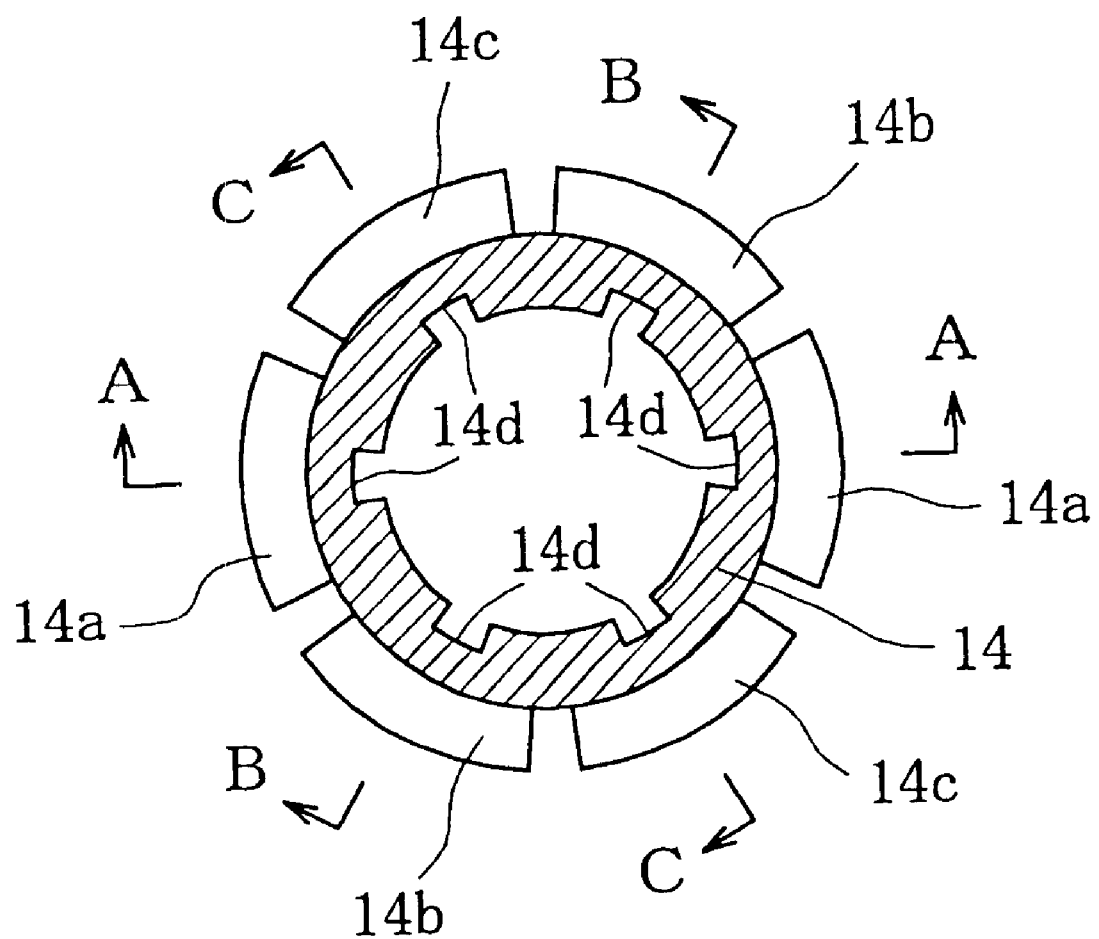
FIG. 4 is a top view of the support.

FIGS. 3A to 3C and FIG. 4 are longitudinally cross-sectional views and a top view of the support 14 respectively. Two pairs of inclined projections 14a, 14b and a pair of inversely inclined projections 14c are formed at positions that a circumference of the support 14 is equally divided into six from the upper end of the outer peripheral surface to a portion near the center of the support 14. Each of the projections is provided with an inclined portion at the tip thereof. The inclined projections 14a, 14b and the inversely inclined projections 14c are arranged at regular intervals in a direction parallel to the central axis of the support 14. The cross-section of each projection of the first inclined projections 14a is, as illustrated in FIG. 3A, a trapezoid of which an upper width is narrower than a lower width. The cross-section of each projection of the second inclined projections 14b is, as illustrated in FIG. 3B, a right-angled triangle. The cross-section of each projection of the inversely inclined projections 14c is, as illustrated in FIG. 3C, a right-angled triangle which is gradually widened toward upside, which is opposite to that of the second inclined projections 14b.

A transmission 16 is capable of engaging with the inclined projections 14a, 14b and the inversely inclined projections 14c of the support 14. And, a ratchet 14e engages with an inner ratchet 17a shown in FIG. 7, and the inner ratchet 17a is integral with a bevel gear to constitute a rotation transmitting means. This construction will be described below.

On the inner portion of the support 14 are cut six channels 14d from upper portion to an intermediate portion thereof. Below the inclined projections 14a, 14b and the inversely inclined projections 14c of the support 14 is a ratchet 14e.

Figure 5A:
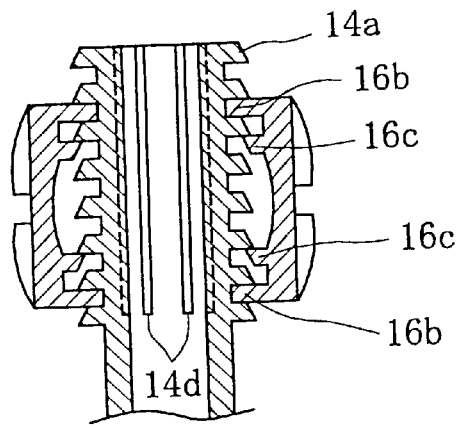
FIGS. 5A to 5C are drawings to show the construction of a transmission.
Figure 5B:
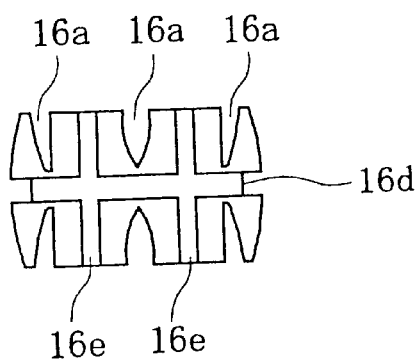
Figure 5C:
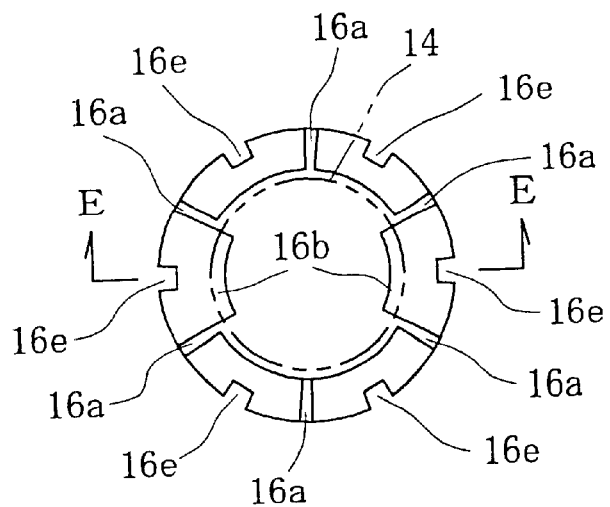

FIGS. 5A to 5c show the construction of the transmission 16, where FIG. 5A is a cross-sectional view observed from E—E of FIG. 5C, FIG. 5B is a front view and FIG. 5C is a top view. As shown in these figures, the transmission 16 has a shape of barrel with a bulging central portion and is made of a resilient metal, synthetic resin or the like. Six notches 16a are formed on the top and bottom end faces at regular intervals, and the end faces are divided into six equal parts. On each of two faces of the six end faces opposite to each other, two pairs of projections 16b, 16c are formed. Other end faces are formed to have a dimension such that the support 14 does not touch the end faces with a play between them.

The projections 16b are positioned at both upper and lower end portions of the transmission 16, and the cross section of the projection 16b is substantially rectangular. The other projections 16c are positioned inside of the transmission 16, and the shape of the cross section of the projection 16c is trapezoid of which width is thinner toward the bottom of FIG. 5A. These projections 16b, 16c engage with the inclined projections 14a, 14b and the inversely inclined projections 14c, which are formed on the support 14, and FIG. 5A, shows that the projections 16b, 16c engage with the inclined projections 14a.

Further, at a central portion, in a vertical direction, of the transmission 16, a drive channel 16d is formed throughout the outer periphery, and six vertical channels 16e extends between the notches 16a in a vertical direction at regular intervals.

Figure 6A:
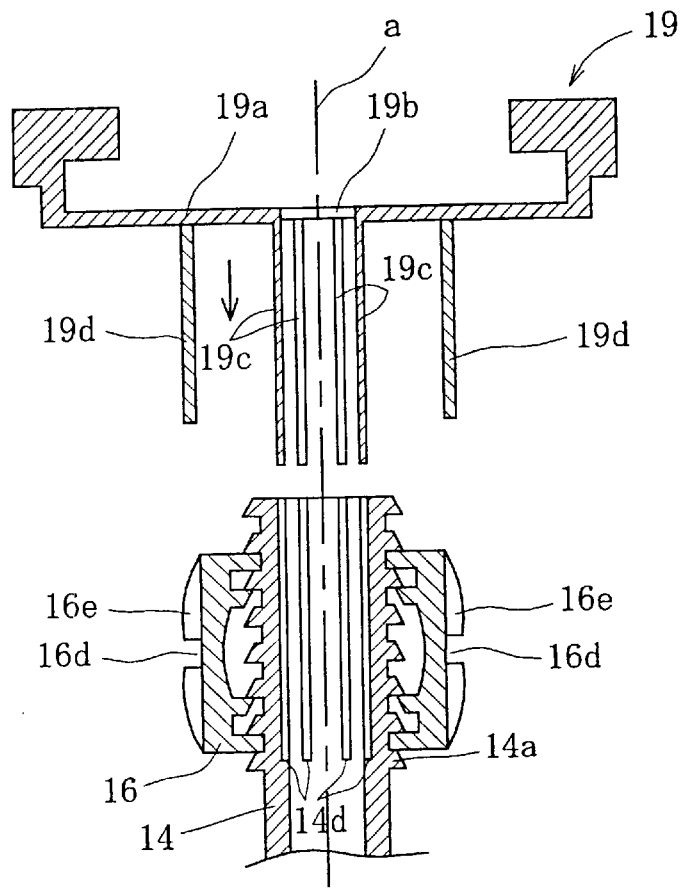
FIGS. 6A and 6B are drawings to show the construction of a switching knob.
Figure 6B:
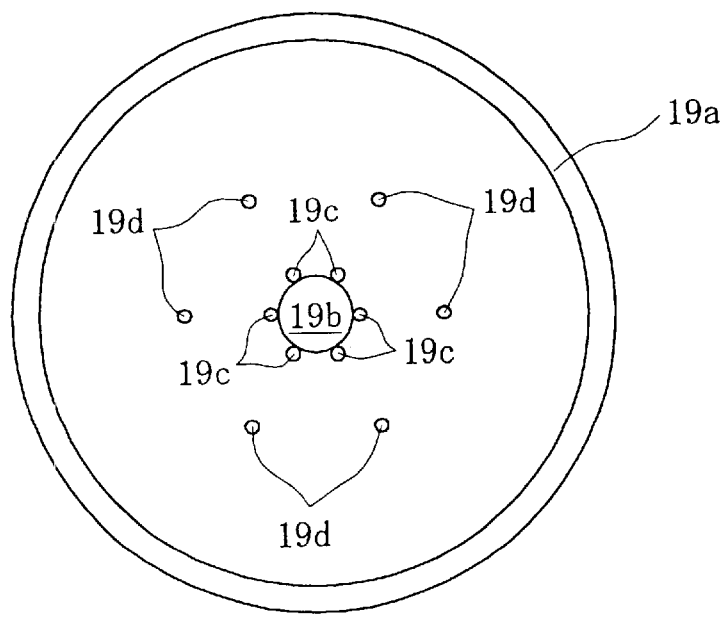

FIGS. 6A and 6B show the construction of a switching knob 19, and FIG. 6A is a longitudinally cross-sectional view, and FIG. 6B is a bottom view. The switching knob 19 is positioned between the upper end of the support 14 and the push button 15 in FIG. 2, and is rotatable about a central axis a of the support 14. The switching knob 19 is provided with a hole 19b adapted to the push button 15 at the center of a disk-shaped base portion 19a, and six engaging bars 19c stand around the hole 19b at regular intervals. Outside of the engaging bar 19c also, six projections 19d stand at regular intervals. The engaging bars 19c, which stand inside, are inserted into the channels 14d formed on the support 14, and the outer projections 19d are inserted into the vertical channels 16e of the transmission 16.

Figure 7A:
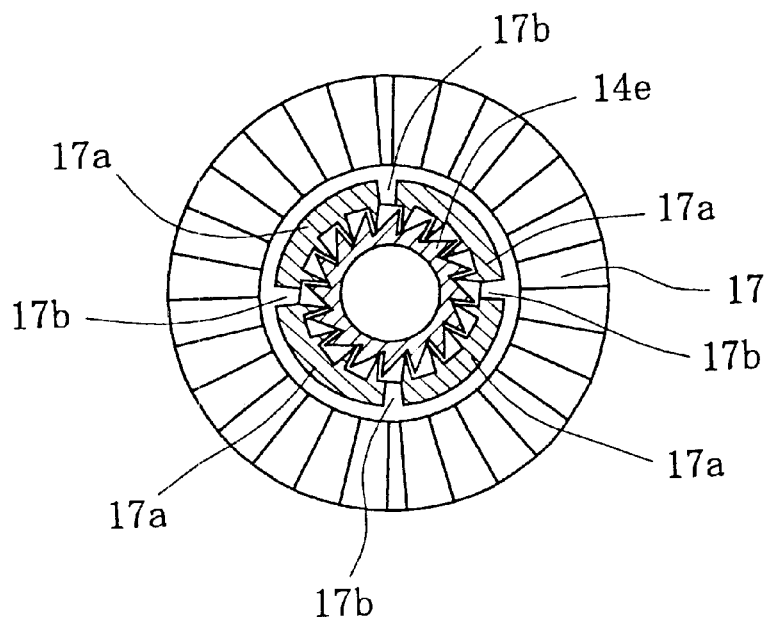
FIGS. 7A and 7B are drawings to show the condition that a bevel gear and the support engage with each other.
Figure 7B:
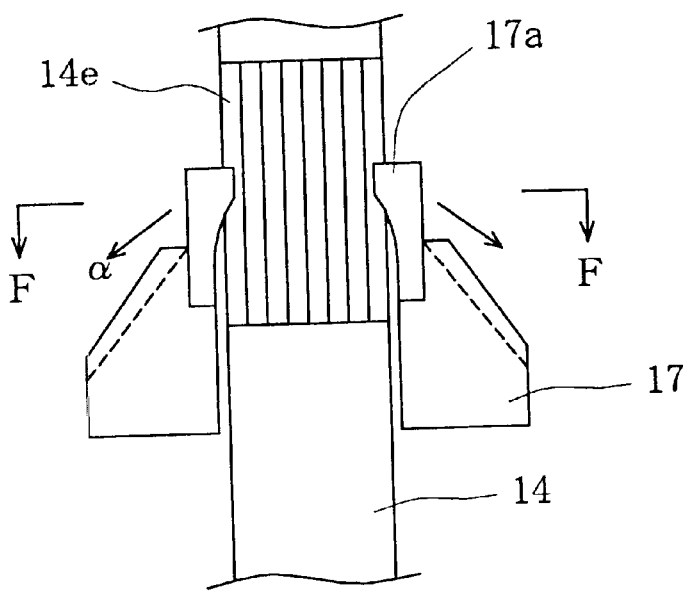

FIGS. 7A and 7B show the condition that a bevel gear 17 and the support 14 engage with each other, and FIG. 7A is a cross-sectional view observed from F—F of FIG. 7B, and FIG. 7B is a longitudinally cross-sectional view. The bevel gear 17 is provided with an inner ratchet 17a that engages with the ratchet 14e at the top of the gear. The inner ratchet 17a is made of a material with resiliency such as synthetic resin different from that of the bevel gear 17 even it is made of metal. It is possible to make the bevel gear 17 and the inner ratchet 17a of the same material if the resiliency of the inner ratchet 17a is ensured as a matter of course.

The inner ratchet 17a is divided into four parts in a circumferential direction by four notches 17b, and is formed to be resilient. The inner ratchet 17a and the ratchet 14e engage with each other to maintain a slight clearance between the bevel gear 17 and the support 14. When the bevel gear 17 rotates counterclockwise in FIG. 7A, the support 14 rotates together with the bevel gear 17, and when the bevel gear 17 rotates clockwise, the support 14 rotates together with the bevel gear 17 at low load only. When the load becomes large, the inner ratchet 17a bends outward in directions indicated by arrows α in FIG. 7B, and the engagement is released, which allows only the bevel gear 17 to slide and rotate but the support 14 not to rotate.

With reference to FIG. 2 again, the head 11 is provided with coaxial two drive shafts. The outer drive shaft 20 is provided with a bevel gear 21 as a rotationally driving means at the tip of the shaft 20, and the bevel gear 21 engages with the bevel gear 17 as a rotationally driving means. The inner drive shaft 22 is provided with a disk 23 at the tip thereof, and an eccentric pin 24 stands on the disk 23, which fits in the drive channel 16d which is a horizontal channel of the transmission 16.

The depth of the drive channel 16d and the length of the eccentric pin 24 are set in such a manner that even if the drive shaft 22 rotates more than one rotation, the state that the tip of the eccentric pin 24 always inserted in the transmission 16 is maintained. When the drive shaft 22 rotates, the eccentric pin 24 also moves on a circle with the drive shaft 22 as the center thereof. Even if the eccentric pin 24 moves in a longitudinal direction of the drive channel 16d, the eccentric pin 24 does not move the transmission 16 at all. However, if the eccentric pin 24 moves in a lateral direction of the drive channel 16d, the transmission 16 moves in a longitudinal direction of the cutting tool 12. In other words, when the drive shaft 22 rotates, the eccentric pin 24 reciprocates the transmission 16 in up and down directions in FIG. 2.

Figure 8A:
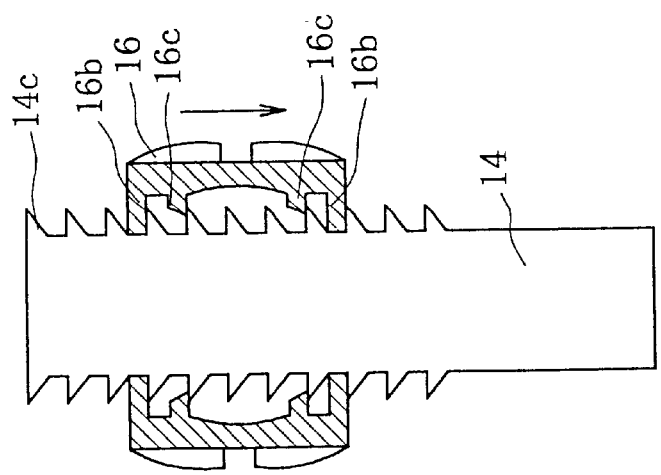
FIGS. 8A to 8C are drawings to explain the movements in a cutting operation by reciprocating a cutting tool.
Figure 8B:
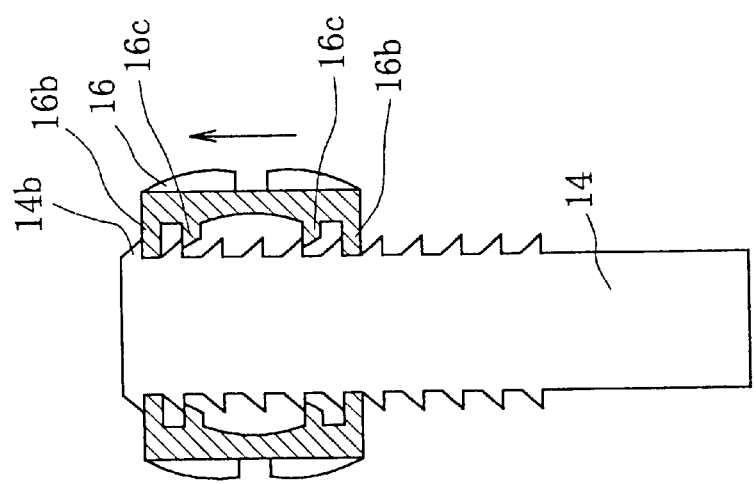
Figure 8C:
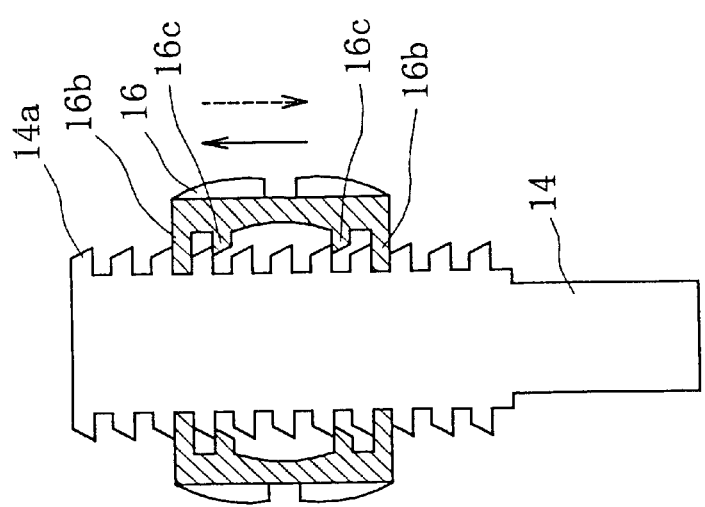
Figure 9A:
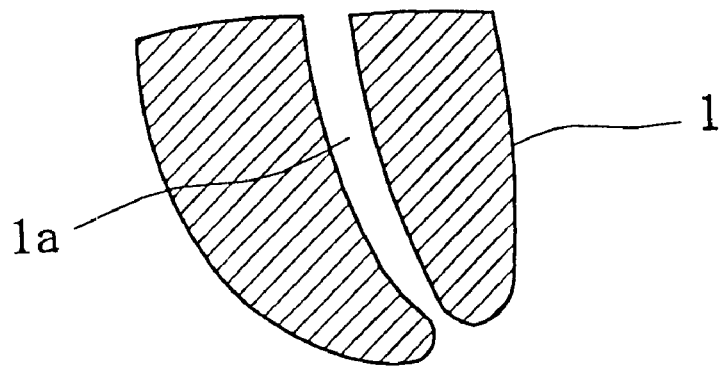
FIGS. 9A and 9B are drawings showing a condition that a ledge is formed in a root canal of a tooth to be cured.
Figure 9B:
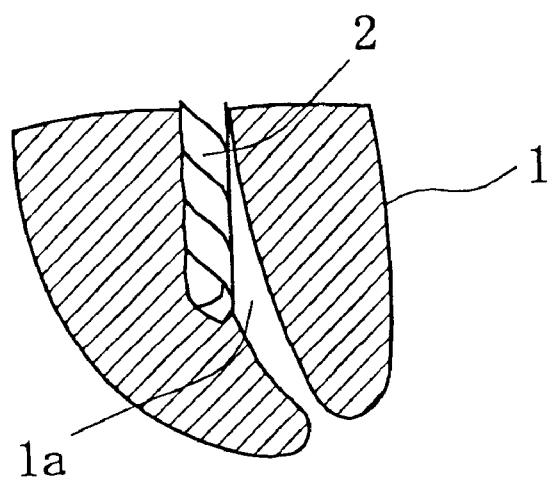
Figure 10A:
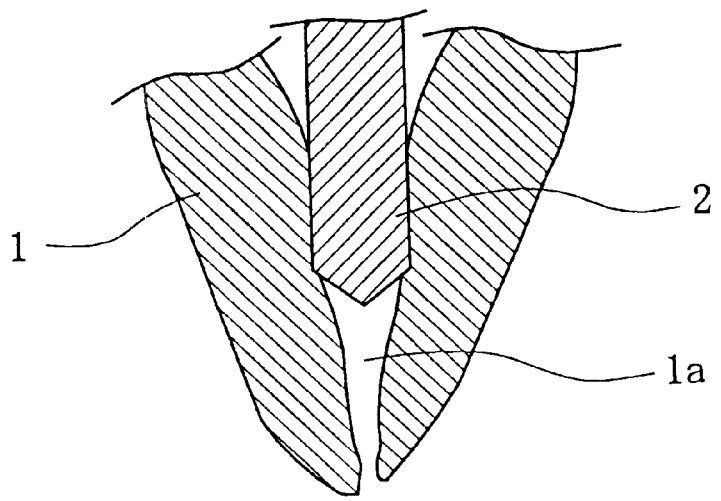
FIGS. 10A and 10B are drawings to explain the necessity that a cutting tool should be changed due to the change of the diameter of a root canal.
Figure 10B:
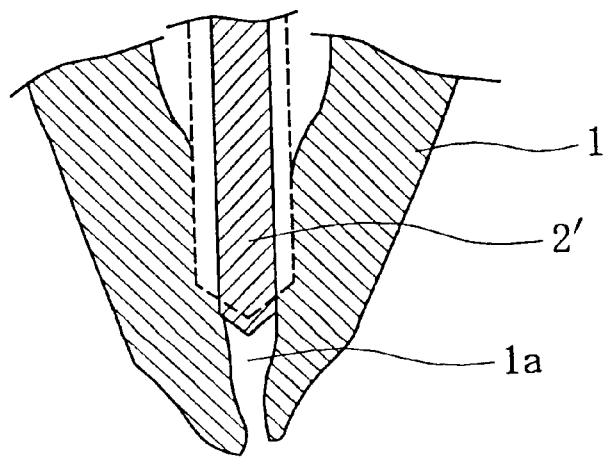

FIGS. 8A to BC are drawings to explain the movements in a cutting operation by reciprocating (back and forth movements) a cutting tool, and FIG. 8A shows a movement in an ordinary cutting operation, FIG. 8B shows a movement when the support 14 is lifted up to the top position to replace the cutting tool, and FIG. 8C shows a movement when the new cutting tool is lowered at a stroke to a desired position.

In case that the ordinary cutting operation of FIG. 8A is selected, the rotation of the drive shaft 22 reciprocates the transmission 16 up and down. Then, the support 14 can securely be lifted upward in FIG. 8A without slippage. However, when the support 14 is lowered, if the load applied to the support 14 is small, the transmission 16 lowers the support 14. On the other hand, when the load is large, the transmission 16 bends outward due to the effects of the notch 16a and the resiliency of the material of the transmission 16 itself, which causes the projections 16b, 16c to slide on the inclined tip faces of the inclined projections 14a to prevent the support 14 from going down.

In case of the ordinary cutting operation shown in FIG. 8A, the projections 16b, 16c of the transmission 16 engage with the inclined projections 14a. At the replacement of the cutting tool 12 illustrated in FIG. 8B, the projections 16b, 16c of the transmission 16 engage with the inclined projection 14b. When the cutting tool 12 is lowered to a prescribed position, the projections 16b, and 16c of the transmission 16 engage with the inversely inclined projections 14c.

Next, a method of switching the conditions shown in FIGS. 8A to 8C will be explained. The switching knob 19 is lifted as shown in FIG. 6A to draw the outer projection 19d from the vertical channel 16e of the transmission 16, and the state that the engaging bars 19c engage with the channels 14d of the support 14 is maintained. Then, a rotation is applied between the transmission 16 and the support 14 such that the angle between them becomes 60° or 120°. As a result, the projections 16b, 16c of the transmission 16 engage the second inclined projection 14b or the third inversely inclined projections 14c. When the transmission 16 engages with desired projections 14b or 14c, the switching knob 19 is lowered to make the engaging bar 19c proceed further into the channel 14d of the support 14, and the outer projection 19d is inserted further into the vertical channel 16e of the transmission 16 to return the original state. Repeating the above motion makes it possible to select any engagement shown in FIGS. 8A to 8C.

Therefore, in FIG. 8A, if the cutting direction is set in a direction that the support 14 goes down, the cutting tool 12 slides without cutting function at an excessive cutting load, which prevents the formation of the ledge and the like. In addition, it is possible to detect the timing that the cutting tool 12 should be replaced with a one rank thinner one since the cutting tool 12 becomes large relative to a root canal.

In cutting a root canal, when the slippage is generated under the condition shown in FIG. 8A, the cutting tool 12 is replaced with a thinner one. For doing this, as described above, the switching knob 19 is lifted and rotated to produce the condition shown in FIG. 8B. Then, when the drive shaft 22 is rotated, and the transmission 16 goes up, the support 14 is lifted during one round trip of the eccentric pin 24 due to the shape of the inclined projection 14b. When the transmission 16 is lowered, the projections 16b, 16c slip on the inclined face of a right-angled triangle of the inclined projection 14b, and the support 14 is not lowered. Shortly, the support 14 is lifted to the top position. Then, the push button 15 is depressed to release the engagement between the cutting tool 12 and the support 14 to remove the cutting tool 12, and the new cutting tool is inserted in the support 14.

Next, the switching knob 19 is lifted again, a rotation is applied between the transmission 16 and the support 14 to produce the condition shown in FIG. 8C. Then, the drive shaft 22 is rotated. This time, the support 14 falls due to the shape of the inversely inclined projections 14c of the support 14, but is prohibited from moving upward, so that the cutting tool 12 proceeds to the bottom. After that, the switching knob 19 is lowered to apply a rotation between the transmission 16 and the support 14 such that the angle between them becomes 60° or 120°, and an ordinary cutting operation is to be carried out under the condition shown in FIG. 8A.

Next, the rotational cutting operation by rotating the support 14 through the rotation of the outer drive shaft 20 will be explained. When the outer drive shaft 20 is rotated, the bevel gear 21 integral with the outer drive shaft 20 rotates, and the rotation is transmitted to the bevel gear 17. The rotation of the bevel gear 17 is transmitted to the ratchet 14e of the support 14 through the inner ratchet 17a.

The rotational cutting operation will be explained hereinafter by taking the case that the cutting tool 12 is rotated clockwise in FIG. 7A. When the rotation of the bevel gear 17 is counterclockwise in FIG. 7A, the inner ratchet 17a and the ratchet 14e securely engage with each other, and the rotation is fully transmitted to the support 14 to allow the rotation of the outer drive shaft 20 to transmit to the cutting tool 12, which allows the cutting tool 12 to rotate in an opposite direction to the cutting operation. On the other hand, when the rotation of the bevel gear 17 is clockwise in FIG. 7A, the inner ratchet 17a and the ratchet 14e engage with each other in a direction that may cause slippage. That is, if the cutting resistance against the support 14 is small, the support 14 rotates, on the contrary, if the resistance is large, the teeth of the inner ratchet 17a rise over the inclined faces of the ratchet 14e, and the resiliency of the inner ratchet 17a causes the inner ratchet 17a to bend in directions of arrows a in FIG. 7B to generate slippage. As a result, the rotation of the inner ratchet 17a is not transmitted to the ratchet 14e.

Therefore, if the direction of the cutting operation is set to be clockwise, when an excessive load is applied to the cutting tool 12, the rotation of the outer drive shaft 20 is not transmitted to the cutting tool 12, which prevents the formation of the ledge and the excessive entering of the cutting tool. Further, it is possible to know the timing that the cutting tool becomes thick relative to the diameter of a root canal, and the cutting tool 12 should be replaced with a thinner one. The method of replacing the cutting tool 12 is the same as that of the cutting operation by the back and forth movements described above.

In the above embodiment, when the teeth of the ratchet 14e are inversely arranged, it is possible to manage the case that the cutting direction is counterclockwise. Further, in the above embodiment, the cutting operations by back and forth movements and rotational movements are independently explained. But, it is a matter of course that the cutting operations by back and forth movements and rotational movements can be carried out at the same time by simultaneously rotating the two drive shafts 20, 22. Still further, in the embodiment described above, the number of notches 16a, vertical channels 16e, channels 14d, engaging bars 19c, and outer projections 19d, and the figures such as the angle that the switching knob 19 rotates are not limited to the above, and are to be changeable as the occasion may demand.

It is a matter of course that besides the above embodiments and modifications, a variety of deformations and alternations are possible within the scope of the claims.

As described above, the dental handpiece according to the present invention comprises: a head; a support mounted in the head to support a cutting tool; and a transmission mounted in the head to transmit driving force to the support; in which the support and the transmission are slidably connected with each other, so that a phenomenon in that an excessive load is applied to a cutting tool, that is, a formation of a ledge is prevented, and it is possible to securely detect the timing that a cutting tool is replaced with a smaller one.

In addition, since a sliding mechanism is mounted in a head of a handpiece, and driving force is transmitted at a position near the object to be cured, there is no influence by intermediate members such as shafts and bearings, which makes it possible to accurately detect the cutting load that produces the slippage. In case of an accident, only the head of the handpiece is to be disassembled, which contributes easy maintenance.

What is claimed is:

1. A dental handpiece comprising:

a head;

a support mounted in the head to support a cutting tool; and a transmission mounted in the head to transmit driving force to the support to drive the support either in a backward or forward direction;

wherein said support and said transmission are slidably connected with each other in such a way that no slippage occurs when a first drive force either in said backward or forward direction is transmitted to the support, whereas slippage occurs when another drive force in a direction opposite to the first drive force is transmitted to the support and a load applied to the cutting tool exceeds a predetermined level.

2. The dental handpiece as claimed in claim 1, wherein said support is cylindrical and is provided with a plurality of first inclined projections that are arranged in a longitudinal direction of an outer periphery of said cylindrical support; said transmission is provided with engaging projections with inclined faces parallel to inclined faces of said plurality of said first inclined projections; and said transmission is provided with resiliency that allows the engaging projections resiliently movable in a direction to depart from the inclined projections.

3. The dental handpiece as claimed in claim 2, wherein a plurality of second inclined projections with inclined faces are provided at positions different from those of said first inclined projections, and said inclined faces of said second inclined projections are different from those of said first inclined projections; and said transmission engages with one of said first and second inclined projections.

4. The dental handpiece as claimed in claim 3, wherein one of said first and second inclined projections engage with said transmission only in one direction and is always slidable in relation to said transmission in a direction opposite to said one direction; and said dental handpiece further includes third inclined projections on said support which engage with said transmission only in a direction opposite to said one direction that said one of said first and second inclined projections engage with said transmission and is slidable in relation to said transmission in a direction reverse to said direction that said third inclined projections engage with said transmission.

5. The dental handpiece as claimed in claim 1, wherein said transmission is movable to a desired position by changing an angle of said support.

6. The dental handpiece as claimed in claim 1, wherein said support is cylindrical and is provided with a ratchet ear at an outer periphery thereof; said dental handpiece further comprises an inner ratchet engaging with said ratchet gear, a rotation transmitting means for rotating the inner ratchet and a rotationally driving means for driving the rotation transmitting means; and said inner ratchet is resiliently displaceable toward a direction to disengage from said ratchet gear.

7. The dental handpiece as claimed in claim 6, wherein said rotation transmitting means and said rotationally driving means are bevel gears that engage with each other.

8. A dental handpiece comprising:

a head;

a cylindrical support mounted in said head;

a plurality of inclined projections and a plurality of inversely inclined projections formed on an outer surface of said support;

a transmission mounted outside of said support, said transmission engaging with one selected from said inclined projections or said inversely inclined projections to transmit driving force to the support;

a ratchet gear formed on an outer periphery of said support; and an inner ratchet engaging with said ratchet gear and is resiliently displaceable toward a direction to disengage from said rachet gear;

wherein when one selected from two groups of inclined projections and said transmission engage with each other, said support is movable in a proceeding direction and is slidable in a retreating direction; when said inversely inclined projections and said transmission engage with each other, said support is movable in a retreating direction and is slidable in a proceeding direction; and when said inner ratchet and said ratchet gear engage with each other, said support is rotatable in a regular direction and is slidable in a direction inverse to said regular direction.

* * * * *